United States Patent [19]

Prasad

[11] Patent Number: 5,808,153
[45] Date of Patent: Sep. 15, 1998

[54] CONVERSION OF N-(4-FLUOROPHENYL)-2-HYDROXY-N-(1-METHYLETHYL) ACETAMIDE ACETATE TO N-4-FLUOROPHENYL)-2-HYDROXY-N-(1-METHYLETHYL) ACETAMIDE

[76] Inventor: Vidyanatha A. Prasad, Bayer Corporation, 100 Bayer Rd., Pittsburgh, Pa. 15205-9741

[21] Appl. No.: 989,151

[22] Filed: Dec. 12, 1997

[51] Int. Cl.⁶ .................................................... C07C 231/12
[52] U.S. Cl. ............................................. 564/203; 564/200
[58] Field of Search ..................................... 564/203, 200, 564/192

[56] References Cited

U.S. PATENT DOCUMENTS

| 4,334,073 | 6/1982 | Diehr | 546/245 |
| 5,101,034 | 3/1992 | Schmidt et al. | 548/136 |

*Primary Examiner*—Brian M. Burn
*Attorney, Agent, or Firm*—Joseph C. Gil; Carol Marmo

[57] ABSTRACT

The present invention provides a process for converting N-(4-fluorophenyl)-2-hydroxy-N-(1-methylethyl)acetamide acetate to N-(4-fluorophenyl)-2-hydroxy-N-(1-methylethyl) acetamide. The process includes the step of hydrolyzing N-(4-fluorophenyl)-2-hydroxy-N-(1-methylethyl)acetamide acetate with water or an aqueous alkali in the presence of an aprotic, aromatic solvent.

21 Claims, No Drawings

CONVERSION OF N-(4-FLUOROPHENYL)-2-HYDROXY-N-(1-METHYLETHYL) ACETAMIDE ACETATE TO N-4-FLUOROPHENYL)-2-HYDROXY-N-(1-METHYLETHYL) ACETAMIDE

TECHNICAL FIELD OF THE INVENTION

The field of the present invention is the synthesis of hydroxy acetamides. More particularly, the invention relates to methods for producing N-(4-fluorophenyl)-2-hydroxy-N-(1-methylethyl)acetamide.

BACKGROUND OF THE INVENTION

Hydroxy acetamides are useful intermediates in the preparation of thiadiazole acetamide herbicides. An exemplary such herbicide is N-(4-fluorophenyl-N-(1-methylethyl)-2-[[5-(trifluoromethyl-1,3,4-thiadiazole-2-yl]oxy]acetamide. (See, e.g., U.S. Pat. No. 5,101,034). This thiadiazole acetamide can be made by reacting N-(4-fluorophenyl)-2-hydroxy-N-(1-methylethyl)acetamide with 2-methylsulfonyl-5-trifluoromethyl-1,3,4-thiadiazole (See, e.g., U.S. Pat. No. 5,101,034). Typically, formation of the N-(4-fluorophenyl)-2-hydroxy-N-(1-methylethyl)acetamide is accomplished by converting the corresponding chloride (i.e., [2-chloro-N-(4-fluorophenyl)-N-(1-methylethyl) acetamide]) to N-(4-fluorophenyl)-2-hydroxy-N-(1-methylethyl)acetamide acetate and then hydrolyzing the acetate intermediate to the final hydroxy acetamide using an alcohol.

U.S. Pat. No. 4,334,073 discloses the production of hydroxy-acetic acid-N-methylamide and hydroxy acetic acid-2-ethyl-piperidine. The methylamide compound is made by reacting chloroacetic acid-N-methylanilide in toluene with sodium acetate and benzyltrimethylammonium chloride to form acetoxy-acetic acid-N-methylanilide and then hydrolyzing that acetate intermediate with methanol to form hydroxy-acetic acid-N-methylamide. A by-product of that reaction, however, is methyl acetate, which must be removed by distillation. In a similar fashion, the piperidine compound is made by reacting chloroacetic acid-N-ethylpiperidine in toluene with sodium acetate and benzyltrimethylammonium chloride to form acetoxy-acetic acid-N-ethylpiperidine and then hydrolyzing that acetate intermediate with methanol to form hydroxy-acetic acid-N-ethylpiperidine. Methyl acetate is also formed as a by-product of that reaction and needs to be removed via distillation.

There is a need in the art, therefore, for a method to produce hydroxy acetamides such as N-(4-fluorophenyl)-2-hydroxy-N-(1-methylethyl)acetamide, which method avoids the formation of methyl acetate and thus, avoids the need for an additional distillation step.

BRIEF SUMMARY OF THE INVENTION

The present invention provides a process for making N-(4-fluorophenyl)-2-hydroxy-N-(1-methylethyl) acetamide. The process converts N-(4-fluorophenyl)-2-hydroxy-N-(1-methylethyl)acetamide acetate to N-(4-fluorophenyl)-2-hydroxy-N-(1-methylethyl)acetamide. The process includes the step of reacting N-(4-fluorophenyl)-2-hydroxy-N-(1-methylethyl)acetamide acetate with an alkali metal base in the presence of water and an aprotic, aromatic solvent.

The N-(4-fluorophenyl)-2-hydroxy-N-(1-methylethyl) acetamide acetate used in the process is produced by reacting 2-chloro-N-(4-fluorophenyl)-N-(1-methylethyl) acetamide with sodium acetate. The reaction of the acetate with base and water in the solvent produces a reaction product having an aqueous phase and an organic phase. The process can further include the step of recovering N-(4-fluorophenyl)-2-hydroxy-N-(1-methylethyl)acetamide from the organic phase.

Preferred solvents include toluene, xylene, cumene or mesitylene. Toluene is most preferred. The base is a water soluble base. Preferably, the base is an alkali metal base such as an alkali metal hydroxide or an alkali metal carbonate. Preferred alkali metals are sodium, potassium and lithium. An especially preferred alkali metal hydroxide is sodium hydroxide. Especially preferred alkali metal carbonates are sodium carbonate and potassium carbonate.

Preferably, the alkali metal base is provided as an aqueous solution containing from about 15 weight percent to about 50 weight percent of the base. More preferably, the aqueous solution contains from about 20 weight percent to about 30 weight percent base. The molar ratio of base to N-(4-fluorophenyl)-2-hydroxy-N-(1-methylethyl)acetamide acetate is from about 1:1 to about 4:1.

The reaction mixture is maintained at a temperature of from about 15° C. to about 50° C. for a period of time sufficient for conversion of the acetate to N-(4-fluorophenyl)-2-hydroxy-N-(1-methylethyl)acetamide. The time will vary with the reaction temperature. When the reaction temperature is about 25° C., the reaction is maintained at that temperature for from about 6 to about 18 hours.

In a preferred embodiment, a process of the invention includes the steps of mixing N-(4-fluorophenyl)-2-hydroxy-N-(1-methylethyl)acetamide acetate in toluene with an aqueous solution of sodium hydroxide to form a reaction product having an aqueous phase and an organic phase, maintaining the reaction product at a temperature of about 25° C. until the N-(4-fluorophenyl)-2-hydroxy-N-(1-methylethyl)acetamide acetate is completely hydrolyzed. This elegant conversion can be monitored using techniques such as gas chromatography (G.C.) or high pressure liquid chromatography (HPLC).

In another aspect, the present invention provides a process for converting N-(4-fluorophenyl)-2-hydroxy-N-(1-methylethyl)acetamide acetate to N-(4-fluorophenyl)-2-hydroxy-N-(1-methylethyl)acetamide. The process includes the step of reacting N-(4-fluorophenyl)-2-hydroxy-N-(1-methylethyl)acetamide acetate with water in the presence of an aprotic, aromatic solvent.

The N-(4-fluorophenyl)-2-hydroxy-N-(1-methylethyl) acetamide acetate used in the process is produced by reacting 2-chloro-N-(4-fluorophenyl)-N-(1-methylethyl) acetamide with sodium acetate. The reaction of the acetate with water in the solvent produces a reaction product having an aqueous phase and an organic phase. The process can further include the step of recovering N-(4-fluorophenyl)-2-hydroxy-N-(1-methylethyl)acetamide from the organic phase. Preferred solvents include toluene, xylene, cumene or mesitylene. Toluene is most preferred.

The reaction mixture is maintained at a temperature of from about 15° C. to about 50° C. for a period of time sufficient for conversion of the acetate to N-(4-fluorophenyl)-2-hydroxy-N-(1-methylethyl)acetamide. The time will vary with the reaction temperature. When the reaction temperature is about 25° C., the reaction is maintained at that temperature for about 40 hours.

In a preferred embodiment, the conversion process includes the steps of mixing N-(4-fluorophenyl)-2-hydroxy- N-(1-methylethyl)acetamide acetate in toluene with water to form a reaction product having an aqueous phase and an organic phase, maintaining the reaction product at a temperature of about 25° C. until the N-(4-fluorophenyl)-2-hydroxy-N-(1-methylethyl)acetamide acetate disappears from the reaction product.

DETAILED DESCRIPTION OF THE INVENTION

I. The Invention

This invention relates to processes for synthesizing N-(4-fluorophenyl)-2-hydroxy-N-(1-methylethyl)acetamide (FOE-hydroxy). The processes provide for (a) converting N-(4-fluorophenyl)-2-hydroxy-N-(1-methylethyl)acetamide acetate (FOE-acetate) to N-(4-fluorophenyl)-2-hydroxy-N-(1-methylethyl)acetamide (FOE-hydroxy) using inorganic bases and (b) converting FOE-acetate to FOE-hydroxy using just water and an aprotic, aromatic solvent.

II. Conversion of N-(4-fluorophenyl)-2-hydroxy-N-(1-methylethyl)acetamide acetate to N-(4-fluorophenyl)-2-hydroxy-N-(1-methylethyl)acetamide using Aqueous Alkali In one aspect, the present invention provides a process for making FOE-hydroxy whereby N-(4-fluorophenyl)-2-hydroxy-N-(1-methylethyl)acetamide acetate (FOE-acetate) is converted to FOE-hydroxy. The conversion involves hydrolyzing the FOE-acetate with an aqueous alkali. The acetate used in the process can be made by any means. Preferably, however, the acetate is made by reacting FOE-chloride with sodium acetate, with or without catalysts.

As set forth herein before, the reaction of sodium acetate and FOE-chloride with the subsequent hydrolysis of the FOE-acetate to FOE-hydroxy is an existing method for making FOE-hydroxy (See, e.g., U.S. Pat. No. 4,334,073, the disclosure of which is incorporated herein by reference). In accordance with that method, hydrolysis of the FOE-acetate is accomplished with the use of an alcohol such as methanol. The use of methanol, however, results in the formation of substantial amounts of the by-product, methyl acetate. This by-product must be removed from the reaction product using a distillation step. The present process avoids the formation of the methyl acetate by-product and, thus, eliminates the distillation step.

A process of the present invention uses an aqueous alkali or base to hydrolyze the FOE-acetate intermediate. More particularly, the process includes the step of reacting FOE-acetate with an alkali metal base in the presence of water and an appropriate organic solvent.

A preferred solvent for use in the process is an aprotic, aromatic organic solvent. Such solvents are well known in the art. Exemplary and preferred such solvents are toluene, xylene, cumene and mesitylene. Toluene is most preferred. The molar ratio of solvent to FOE-acetate is from about 4:1 to about 8:1.

The base used in the process is a water soluble base. Preferably, the base is an alkali metal base such as an alkali metal hydroxide or an alkali metal carbonate. Preferred alkali metals are sodium, potassium and lithium. An especially preferred alkali metal hydroxide is sodium hydroxide. Especially preferred alkali metal carbonates are sodium carbonate and potassium carbonate.

Preferably, the alkali metal base is provided as an aqueous solution containing from about 15 weight percent to about 50 weight percent of the base. More preferably, the aqueous solution contains from about 20 weight percent to about 30 weight percent base. The molar ratio of base to FOE-acetate is from about 1:1 to about 4:1.

The reaction is initiated by mixing the FOE-acetate in the solvent (e.g., toluene) with base and water. The reaction mixture, thus, contains both an aqueous phase and an organic phase. The total amount of base can be added at a single time or, preferably, in aliquots over 1 to 2 hours. The molar ratio of added water to FOE-acetate is from about 25:1 to about 50:1.

The reaction mixture is heated until hydrolysis of the FOE-acetate is substantially complete. The total time needed for completion of the reaction varies, as is well known in the art, with reaction temperature. Typically, the reaction mixture is maintained at a temperature of from about 15° C. to about 50° C. An especially preferred reaction temperature is room temperature (about 25° C.). When the reaction temperature is about 25° C., the reaction is maintained at that temperature for from about 6 to about 18 hours (overnight).

The process can further include the step of recovering FOE-hydroxy from the organic phase. Means for recovering FOE-hydroxy are the same as set forth above in Section II.

In a preferred embodiment, a process of the invention includes the steps of mixing FOE-acetate in toluene with an aqueous solution of sodium hydroxide to form a reaction product having an aqueous phase and an organic phase, maintaining the reaction product at a temperature of about 25° C. until the FOE-acetate is completely hydrolyzed, and recovering the FOE-hydroxy.

III. Conversion of N-(4-fluorophenyl)-2-hydroxy-N-(1-methylethyl)acetamide acetate to N-(4-fluorophenyl)-2-hydroxy-N-(1-methylethyl)acetamide via Hydrolysis in Solvent and Water The present invention provides an additional means for converting FOE-acetate to FOE-hydroxy, which means avoids the use of both methanol and aqueous alkali. In accordance with this process, FOE-acetate is hydrolyzed to FOE-hydroxy with water in the presence of solvent. The by-product is acetic acid, which is easily biodegradable resulting in no salt load of sodium acetate in the waste stream. Preferred solvents are the same as set forth above. Toluene is the most preferred solvent.

Hydrolysis is carried out by dissolving or otherwise suspending FOE-acetate in the solvent. Preferred ratios of solvent to FOE-acetate are set forth above. The FOE-acetate in solvent is then mixed with water in the molar ratio of from about 5 to about 30 moles of water per mole of FOE-acetate. Preferably, that molar ratio is from about 25:1 to about 30:1. The mixture of FOE-acetate, solvent and water is then maintained at a suitable temperature for hydrolysis for a period of time sufficient for hydrolysis of the FOE-acetate to FOE-hydroxy. The time required for substantially complete hydrolysis will vary, as is well known in the art, on the hydrolysis temperature used. Typically, hydrolysis with water is carried out at a temperature of from about 20° C. to about 50° C. More preferably, the temperature is from about 20° C. to about 30° C. This temperature range corresponds to ambient, room temperature conditions. When hydrolysis is carried out at ambient, room temperature, the time required for substantially complete hydrolysis of the FOE-acetate is from about 35 to about 45 hours. The progress of the hydrolysis reaction can be monitored using GC or HPLC analysis and terminated upon disappearance of FOE-acetate. FOE-hydroxy made in accordance with this hydrolysis is recovered and isolated using means well known in the art such as set forth above.

The Examples that follow illustrate preferred embodiments of the present invention and are not limiting of the specification and claims in any way.

EXAMPLES

Example 1

Conversion of N-(4-fluorophenyl)-2-hydroxy-N-(1-methylethyl)acetamide acetate to N-(4-fluorophenyl)-2- hydroxy-N-(1-methylethyl)acetamide Using Aqueous Alkali and Toluene 253.24 Grams (1.0 mole) of FOE-acetate were placed in a flask. 600 Grams of toluene were added with agitation to the flask at ambient temperature (25° C.). 600 Grams of water were then added to the agitated mixture, followed by the addition of 160 Grams of 50% NaOH (2 moles). The mixture was stirred at various temperatures (25° C. to 80° C.) for various times (4 to 10 hours).

G.C. analysis and HPLC analysis of the organic phase indicated completion of the reaction. The phases were separated and the aqueous phase washed with 100 Grams toluene. The toluene wash was combined with the organic phase. Solvent was removed via vacuum stripping and FOE-hydroxy was isolated via flaking. The results are summarized in the table below.

| Reaction Temp | Reaction Time | A. I. % | Net Yield % |
|---|---|---|---|
| 25° C. | 10 hrs | 98.2 | 97.5 |
| 40° C. | 8 hrs | 98.0 | 97.4 |
| 60° C. | 6 hrs | 97.8 | 96.2 |
| 80° C. | 4 hrs | 96.6 | 95.5 |

EXAMPLE 2

Conversion of N-(4-fluorophenyl)-2-hydroxy-N-(1-methylethyl)acetamide acetate to N-(4-fluorophenyl)-2-hydroxy-N-(1-methylethyl)acetamide Using Water and Toluene 253.24 Grams (1.0 mole) of FOE-acetate were placed in a flask. About 600 Grams of toluene were added with agitation at ambient temperature (25° C.). About 600 Grams of water were then added to the agitated mixture at 25° C. The mixture was agitated at various temperatures (25° C.–80° C.) for various times (12–48 hours).

G.C. analysis and HPLC analysis of the organic phase indicated completion of the reaction (at 25° C., ca. 50% completion was observed at the end of 24 hrs). The phases were separated and the aqueous phase washed with 100 grams of toluene. The toluene wash was combined with the organic phase. Solvent was removed through vacuum stripping and FOE-hydroxy isolated via flaking. The results are shown in the table below.

| Reaction Temp | Reaction Time | A. I. % | Net Yield % |
|---|---|---|---|
| 25° C. | 48 hrs | 98.4 | 97.8 |
| 40° C. | 36 hrs | 98.4 | 97.6 |
| 60° C. | 24 hrs | 98.2 | 97.1 |
| 80° C. | 12 hrs | 98.0 | 96.8 |

Although the invention has been described in detail in the foregoing for the purpose of illustration, it is be understood that such detail is solely for that purpose and that variations can be made therein by those skilled in the art without departing from the spirit and scope of the invention except as it may be limited by the claims.

What is claimed is:

1. A process for making N-(4-fluorophenyl)-2-hydroxy-N-(1-methylethyl)acetamide comprising the steps of:
    (a) reacting N-(4-fluorophenyl)-2-hydroxy-N-(1-methylethyl)acetamide acetate with an alkali metal base in the presence of water and an aprotic, aromatic solvent to form a reaction product having an aqueous phase and an organic phase; and
    (b) recovering N-(4-fluorophenyl)-2-hydroxy-N-(1-methylethyl)acetamide from the organic phase.

2. The process of claim 1 wherein the solvent is toluene, xylene, cumene or mesitylene.

3. The process of claim 2 wherein the solvent is toluene.

4. The process of claim 1 wherein the alkali metal base is an alkali metal hydroxide or an alkali metal carbonate.

5. The process of claim 4 wherein the alkali metal is sodium, potassium or lithium.

6. The process of claim 5 wherein the alkali metal hydroxide is sodium hydroxide.

7. The process of claim 5 wherein the alkali metal carbonate is potassium carbonate.

8. The process of claim 1 wherein the molar ratio of alkali metal base to N-(4-fluorophenyl)-2-hydroxy-N-(1-methylethyl)acetamide acetate is from about 1:1 to about 4:1.

9. The process of claim 1 wherein the aqueous alkali metal base is an aqueous solution of from about 1 weight percent to about 50 weight percent alkali metal base.

10. The process of claim 9 wherein the alkali metal base is sodium hydroxide.

11. The process of claim 1 wherein N-(4-fluorophenyl)-2-hydroxy-N-(1-methylethyl)acetamide acetate in toluene is mixed with an aqueous solution of sodium hydroxide to form a reaction product and the reaction product maintained at a temperature of from about 20° C. to about 45° C. until the N-(4-fluorophenyl)-2-hydroxy-N-(1-methylethyl) acetamide acetate disappears from the reaction product.

12. The process of claim 1 wherein the N-(4-fluorophenyl)-2-hydroxy-N-(1-methylethyl)acetamide acetate is formed by reacting 2-chloro-N-(4-fluorophenyl)-N-(1-methylethyl)acetamide with sodium acetate.

13. A process of converting N-(4-fluorophenyl)-2-hydroxy-N-(1-methylethyl)acetamide acetate to N-(4-fluorophenyl)-2-hydroxy-N-(1-methylethyl)acetamide comprising the step of hydrolyzing N-(4-fluorophenyl)-2-hydroxy-N-(1-methylethyl) acetamide acetate with water in the presence of an aprotic, aromatic solvent.

14. The process of claim 13 wherein the solvent is toluene, cumene, xylene or mesitylene.

15. The process of claim 14 wherein the solvent is toluene.

16. The process of claim 15 wherein the molar ratio of toluene to N-(4-fluorophenyl)-2-hydroxy-N-(1-methylethyl) acetamide acetate is from about 3:1 to about 10:1.

17. The process of claim 16 wherein the molar ratio of toluene to N-(4-fluorophenyl)-2-hydroxy-N-(1-methylethyl) acetamide acetate is from about 4:1 to about 5:1.

18. The process of claim 13 wherein the molar ratio of water to N-(4-fluorophenyl)-2-hydroxy-N-(1-methylethyl) acetamide acetate is from about 10:1 about 30:1.

19. The process of claim 18 wherein the molar ratio of water to N-(4-fluorophenyl)-2-hydroxy-N-(1-methylethyl) acetamide acetate is from about 20:1 to about 30:1.

20. The process of claim 13 wherein hydrolysis is carried out at a temperature of from about 20° C. to about 30° C. for from about 35 to about 45 hours.

21. A process of converting N-(4-fluorophenyl)-2-hydroxy-N-(1-methylethyl)acetamide acetate to N-(4-fluorophenyl)-2-hydroxy-N-(1-methylethyl)acetamide comprising the steps of:
    (a) adding water to a mixture of N-(4-fluorophenyl)-2-hydroxy-N-(1-methylethyl)acetamide acetate in toluene to form a reaction mixture having an aqueous phase and an organic phase;
    (b) heating the reaction mixture from step (a) to a temperature of from about 20° C. to about 30° C. for from about 35 hours to about 45 hours;
    (c) separating the organic phase from the aqueous phase; and
    (d) recovering N-(4-fluorophenyl)-2-hydroxy-N-(1-methylethyl)acetamide from the organic phase.

* * * * *